United States Patent [19]

Atwal

[11] Patent Number: 4,746,656

[45] Date of Patent: May 24, 1988

[54] 1,2,4,7-TETRAHYDRO-2-OXOPYRAZOLO[1,5-A]PYRIMIDINE DERIVATIVES

[75] Inventor: Karnail Atwal, Cranbury, N.J.

[73] Assignee: E. R. Squibb & Sons, Inc., Princeton, N.J.

[21] Appl. No.: 887,397

[22] Filed: Jul. 21, 1986

[51] Int. Cl.⁴ .................. C07D 487/04; C07D 403/14; C07D 417/14; A61K 31/505

[52] U.S. Cl. .............................. 514/212; 514/228.5; 514/232.5; 514/233.2; 514/255; 514/258; 540/600; 544/61; 544/117; 544/281

[58] Field of Search .................. 544/281, 117, 61; 514/258, 212, 222, 233, 234, 236, 255; 540/600

[56] References Cited

U.S. PATENT DOCUMENTS 2,593,890  4/1952  Kellog ............................. 544/281

FOREIGN PATENT DOCUMENTS 0163240 12/1985 European Pat. Off. .
599891  3/1948 United Kingdom ................ 544/281

OTHER PUBLICATIONS

C. F. H. Allen et al., J. Org. Chem., 24, 779–787 (1959).

*Primary Examiner*—Nicholas S. Rizzo
*Assistant Examiner*—E. Bernhardt
*Attorney, Agent, or Firm*—Lawrence S. Levinson; Donald J. Barrack

[57] ABSTRACT

Cardiovascular activity is exhibited by compounds having the formula

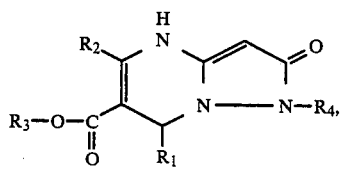

or a pharmaceutically acceptable salt thereof, wherein $R_1$ is aryl or heterocyclo;

$R_2$ is hydrogen, alkyl, alkenyl, alkynyl, cycloalkyl, aryl, $-(CH_2)_n-Y_1$, or halo substituted alkyl;

$R_3$ is hydrogen, alkyl, cycloalkyl, aryl, heterocyclo, $-(CH_2)_n-Y_2$, $-(CH_2)_p-Y_3$, or halo substituted alkyl;

$R_4$ is hydrogen, alkyl, alkenyl, alkynyl, $-(CH_2)_n-Y_2$, $-(CH_2)_p-Y_3$, halo substituted alkyl, or

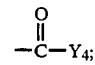

$Y_1$ is cycloalkyl, aryl, heterocyclo, hydroxyl, alkoxy, aryl—$(CH_2)_m$—O—, mercapto, alkylthio, aryl—$(CH_2)_m$—S—, amino, substituted amino, carbamoyl,

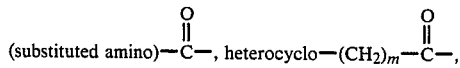

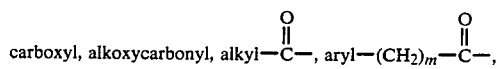

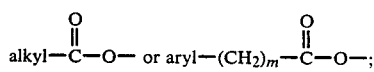

$Y_2$ is cycloalkyl, aryl, heterocyclo, carbamoyl,

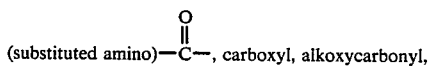

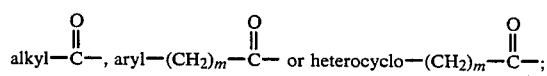

$Y_3$ is hydroxyl, alkoxy, aryl—$(CH_2)_m$—O—, mercapto, alkylthio, aryl—$(CH_2)_m$—S—,

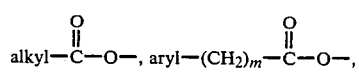

amino, or substituted amino;
$Y_4$ is alkyl, cycloalkyl, aryl, heterocyclo, $-(CH_2)_n-Y_1$ or halo substituted alkyl;
m is 0 or an integer of 1 to 6;
n is an integer of 1 to 6; and
p is an integer of 2 to 6.

18 Claims, No Drawings

1,2,4,7-TETRAHYDRO-2-OXOPYRAZOLO[1,5-A]PYRIMIDINE DERIVATIVES

BRIEF DESCRIPTION OF THE INVENTION

Compounds having the formula

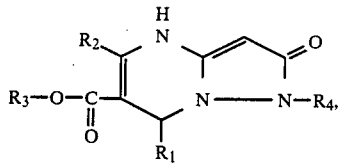

and the pharmaceutically acceptable salts thereof, are cardiovascular agents. In formula I, and throughout the specification, the symbols are as defined below.

$R_1$ is aryl or heterocyclo;

$R_2$ is hydrogen, alkyl, alkenyl, alkynyl, cycloalkyl, aryl, —$(CH_2)_n$—$Y_1$, or halo substituted alkyl;

$R_3$ is hydrogen, alkyl, cycloalkyl, aryl, heterocyclo, —$(CH_2)_n$—$Y_2$, —$(CH_2)_p$—$Y_3$, or halo substituted alkyl;

$R_4$ is hydrogen, alkyl, alkenyl, alkynyl, —$(CH_2)_n$—$Y_2$, —$(CH_2)_p$—$Y_3$, halo substituted alkyl, or

$Y_1$ is cycloalkyl, aryl, heterocyclo, hydroxyl, alkoxy, aryl—$(CH_2)_m$—O—, mercapto, alkylthio, aryl—$(CH_2)_m$—S—, amino, substituted amino, carbamoyl,

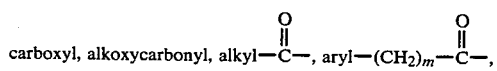

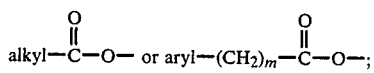

$Y_2$ is cycloalkyl, aryl, heterocyclo, carbamoyl,

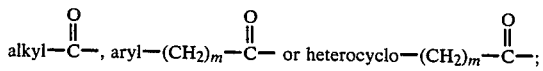

$Y_3$ is hydroxyl, alkoxy, aryl—$(CH_2)_m$—O—, mercapto, alkylthio, aryl—$(CH_2)_m$—S—,

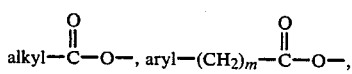

amino, or substituted amino;

$Y_4$ is alkyl, cycloalkyl, aryl, heterocyclo, —$(CH_2)_n$—$Y_1$ or halo substituted alkyl;

m is 0 or an integer of 1 to 6;

n is an integer of 1 to 6; and p is an integer of 2 to 6.

Listed below are definitions of various terms used to describe the compounds of this invention. These definitions apply to the terms as they are used throughout the specification (unless they are otherwise limited in specific instances) either individually or as part of a larger group.

The terms "alkyl" and "alkoxy" refer to both straight and branched chain groups. Those groups having 1 to 8 carbon atoms are preferred.

The term "halo substituted alkyl" refers to alkyl groups (as described above) in which one or more hydrogens have been replaced by chloro, bromo or fluoro groups. Exemplary groups are trifluoromethyl, which is preferred, pentafluoroethyl, 2,2,2-trichloroethyl, chloromethyl, bromomethyl, etc.

The term "aryl" refers to phenyl and substituted phenyl. Exemplary substituted phenyl groups are phenyl groups substituted with one, two or three alkyl, alkoxy, alkylthio, halo, nitro, cyano, hydroxy, amino, alkylamino, dialkylamino, trifluoromethyl, isothiocyanato, isocyanato, or difluoromethoxy groups.

The terms "alkenyl" and "alkynyl" refer to both straight and branched chain groups. Those groups having 2 to 8 carbon atoms are preferred.

The term "cycloalkyl" refers to those groups having 3, 4, 5, 6 or 7 carbon atoms.

The term "halo" refers to chloro, bromo, fluoro and iodo.

The term "heterocyclo" refers to fully saturated, partially saturated or unsaturated rings of 5 or 6 atoms containing one or two oxygen or sulfur atoms and/or one to four nitrogen atoms provided that the total number of hetero atoms in the ring is 4 or less. The heterocyclo ring is attached by way of an available carbon atom. Preferred monocyclic heterocyclo groups include 2- and 3-thienyl, 2- and 3-furyl, 2- and 3-pyrrolyl, 2-, 3- and 4-pyridyl, 2-, 4- and 5-imidazolyl, 2- and 3-pyrrolidinyl, 2-, 3- and 4-piperidinyl, and 2-, 3- and 4-azepinyl. The term heterocyclo also includes bicyclic rings wherein the five or six membered ring containing oxygen, sulfur and nitrogen atoms as defined above is fused to a benzene ring and the bicyclic ring is attached by way of an available carbon atom in the benzene ring. Preferred bicyclic heterocyclo groups include 4, 5, 6 or 7-indolyl, 4, 5, 6 or 7-isoindolyl, 5, 6, 7 or 8-quinolinyl, 5, 6, 7 or 8-isoquinolinyl, 4, 5, 6 or 7-benzothiazolyl, 4, 5, 6 or 7-benzoxazolyl, 4, 5, 6 or 7-benzimidazolyl, 4, 5, 6 or 7-benzoxadiazolyl, and 4, 5, 6 or 7-benzofurazanyl.

The term heterocyclo also includes such monocyclic and bicyclic rings as defined above substituted with one, or more, alkyl, arylalkyl, diarylalkyl, alkylthio, alkoxy, halo, nitro, oxo, cyano, hydroxy, amino, alkylamino, dialkylamino, trifluoromethyl, isocyanato, isothiocyanato or difluoromethoxy groups.

The term "substituted amino" refers to a group of the formula —$NZ_1Z_2$ wherein $Z_1$ is hydrogen, alkyl, or aryl—$(CH_2)_m$— and $Z_2$ is alkyl or aryl—$(CH_2)_m$— or $Z_1$ and $Z_2$ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, or 1-pyrrolidinyl, 1-piperidinyl, or 1-azepinyl substituted with alkyl, alkoxy, alkylthio, halo, trifluoromethyl or hydroxy.

DETAILED DESCRIPTION OF THE INVENTION

The compounds of formula I, and the pharmaceutically acceptable salts thereof, are cardiovascular agents. They act as calcium entry blocking vasodilators and are especially useful as hypotensive agents. Thus, by the administration of a composition containing one (or a combination) of the compounds of this invention, the blood pressure of a hypertensive mammalian (e.g., human) host is reduced. A single dose, or two to four divided daily doses, provided on a basis of about 0.1 to 100 milligrams per kilogram of body weight per day, preferably from about 1 to about 50 milligrams per kilogram per day, is appropriate to reduce blood pressure. The substance is preferably administered orally, but parenteral routes such as the subcutaneous, intramuscular or intravenous routes can also be employed.

As a result of the calcium entry blocking activity of the compounds of formula I, and the pharmaceutically acceptable salts thereof, it is believed that such compounds in addition to being hypotensive agents may also be useful as antiarrhythmic agents, anti-anginal agents, antifibrillatory agents, anti-asthmatic agents, and in limiting myocardial infarction.

The compounds of this invention can also be formulated in combination with a diuretic, or a beta-adrenergic agent, or angiotensin converting enzyme inhibitor. Suitable diuretics include the thiazide diuretics such as hydrochlorothiazide and bendroflumethiazide, suitable beta-adrenergic agents include nadolol, and suitable angiotensin converting enzyme inhibitors include captopril.

The compounds of formula I can be formulated for use in the reduction of blood pressure in compositions such as tablets, capsules or elixirs for oral administration, or in sterile solutions or suspensions for parenteral administration. About 10 to 500 milligrams of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The products of formula I wherein $R_4$ is hydrogen can be prepared by reacting 3-amino-5-pyrazolone with a keto ester compound having the formula

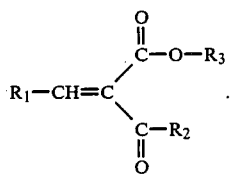

II

The reaction is preferably heated in the presence of an organic solvent such as dimethylformamide.

In those instances wherein the keto ester compound of formula II contains reactive substituents not meant to participate in the reaction, it may be necessary to first protect these functional groups, carry out the desired reaction, and then remove the protecting group.

The products of formula I wherein $R_4$ is alkyl, alkenyl, alkynyl, —$(CH_2)_n$—$Y_2$, —$(CH_2)_p$—$Y_3$ or halo substituted alkyl can be prepared by alkylating the corresponding product of formula I wherein $R_4$ is hydrogen with the appropriate alkylating agent and a base such as sodium hydride.

The products of formula I wherein $R_4$ is

can be prepared by acylating the corresponding product of formula I wherein $R_4$ is hydrogen using, for example, an acyl halide in the presence of an organic base.

The compounds of formula I that contain a basic or acid group form acid addition and basic salts with a variety of inorganic and organic acids and bases. The pharmaceutically acceptable salts are preferred, although other salts may also be useful in isolating or purifying the product. Such pharmaceutically acceptable acid addition salts include those formed with hydrochloric acid, methanesulfonic acid, toluenesulfonic acid, sulfuric acid, acetic acid, maleic acid, etc. Pharmaceutically acceptable basic salts include alkali metal salts (e.g., sodium, potassium and lithium) and alkaline earth metal salts (e.g., calcium and magnesium). The salts can be obtained by reacting the product with an equivalent amount of the acid in a medium in which the salt precipitates.

Preferred compounds of this invention are those wherein:

$R_2$ is alkyl (especially methyl), $R_3$ is alkyl and $R_4$ is hydrogen.

The following examples are specific embodiments of this invention.

EXAMPLE 1

7-(2,3-Dichlorophenyl)-1,2,4,7-tetrahydro-5-methyl-2-oxopyrazolo[1,5-a]pyrimidine-6-carboxylic acid, ethyl ester A solution of 2-[(2,3-dichlorophenyl)methylene]-3-oxobutanoic acid, ethyl ester (2.8 g; 10.0 mmole) in dimethylformamide (7 ml) was treated with 3-amino-5-pyrazolone (990 mg) and the resulting mixture was heated at 65° C.±5° for 15 hours. The reaction mixture was allowed to cool to room temperature and then diluted with ethyl acetate. The solution was washed with water, brine, and dried over anhydrous magnesium sulfate. Evaporation of the solvent provided a foam which was purified by flash chromatography (7% methanol in dichloromethane). The product was crystallized from acetonitrile-isopropyl ether to provide the title compound as a solid (1.42 g; melting point 213°–218° C.; sinters above 155° C.).

Analysis Calc'd. for $C_{16}H_{15}Cl_2N_3O_3$: C, 52.19; H, 4.11; N, 11.41; Cl, 19.25. Found: C, 52.23; H, 4.11; N, 11.28; Cl, 19.23

EXAMPLE 2

1,2,4,7-Tetrahydro-5-methyl-7-(3-nitrophenyl)-2-oxopyrazolo[1,5-a]pyrimdine-6-carboxylic acid, 1-methylethyl ester A mixture of 3-amino-5-pyrazolone (3.57 g; 36.1 mmole) and 2-[(3-nitrophenyl)methylene]-3-oxobutanoic acid, 1-methylethyl ester (10.0 g; 36.1 mmole) in dry dimethylformamide (30 ml) was heated at 70° C. under argon for 24 hours. The reaction mixture was allowed to cool to room temperature and then diluted with ether. The resultant precipitate was filtered off and recrystallized from isopropanol to provide the title compound in crystalline form (4.23 g; melting point 254°–256° C.).

Analysis Calc'd. for $C_{17}H_{18}N_4O_5$: C, 56.98; H, 5.06; N, 15.63. Found: C, 57.18; H, 5.10; N, 15.70.

EXAMPLE 3

1,2,4,7-Tetrahydro-5-methyl-7-(3-nitrophenyl)-2-oxo-1-(phenylmethyl)pyrazolo[1,5-a]pyrimidine-6-carboxylic acid, 1-methylethyl ester To a suspension of sodium hydride (30 mg; 60% dispersion; 0.75 mmole) in dry dimethylformamide (4 ml) was added 1,2,4,7-tetrahydro-5-methyl-7-(3-nitrophenyl)-2-oxopyrazolo[1,5-a]pyrimidine-6-carboxylic acid, 1-methylethyl ester (180 mg; 0.5 mmole) in dimethylformamide (3 ml) at 0° C. under argon. The orange reaction mixture was allowed to stir at 0° C. for 30 minutes and benzyl bromide (70 μl; 0.6 mmole) was then added. The reaction was stirred at room temperature for one hour and then quenched with water. The resulting solution was extracted with ethyl acetate and the combined extracts were washed with water, sodium bicarbonate and brine. After drying over anhydrous magnesium sulfate, the solvent was evaporated to give a foam which was purified by preparative thin layer chromatography (40% ethyl acetate in hexanes) and the product was crystallized from dichloromethane-isopropyl ether to give a solid, melting point 183.5°–185° C.

Analysis Calc'd.: C, 64.27; H, 5.39; N, 12.49. Found: C, 64.49; H, 5.69; N, 12.15

EXAMPLE 4

1-Benzoyl-1,2,4,7-tetrahydro-5-methyl-7-(3-nitrophenyl)-2-oxopyrazolo[1,5-a]pyrimidine-6-carboxylic acid, 1-methylethyl ester A suspension of 1,2,4,7-tetrahydro-5-methyl-7-(3-nitrophenyl)-2-oxopyrazolo[1,5-a]pyrimidine-6-carboxylic acid, 1-methylethyl ester (36 mg; 0.1 mmole) in dichloromethane (2 ml) and pyridine (1 ml) under argon was treated with benzoyl chloride (28 mg; 0.2 mmole). The reaction was allowed to stir for 30 minutes and then diluted with ethyl acetate. The resulting solution was washed with 1N hydrochloric acid, water, sodium bicarbonate and brine. It was dried over anhydrous magnesium sulfate and evaporated. The residue was purified by preparative thin layer chromatography (40% acetone in hexanes) and the product was crystallized from absolute ethanol to provide a solid, melting point 201°–203° C.

Analysis Calc'd.: C, 62.33; H, 4.79; N, 12.11 Found: C, 62.33; H, 4.92; N, 12.00.

Additional compounds falling within the scope of this invention are:

1,2,4,7-Tetrahydro-5-methyl-1-[3-[methyl(phenylmethyl)amino]propyl]-7-(3-nitrophenyl)-2-oxopyrazolo[1,5-a]pyrimidine-6-carboxylic acid, 1-methylethyl ester 1,2,4,7-Tetrahydro-5-methyl-7-(3-nitrophenyl)-2-oxopyrazolo[1,5-a]pyrimidine-6-carboxylic acid, 2-[methyl(phenylmethyl)amino]ethyl ester 1,2,4,7-Tetrahydro-1,5-dimethyl-7-(3-nitrophenyl)-2-oxopyrazolo[1,5-a]pyrimidine-6-carboxylic acid, ethyl ester 1,2,4,7-Tetrahydro-5-methyl-7-(2-nitrophenyl)-2-oxopyrazolo[1,5-a]pyrimidine-6-carboxylic acid, ethyl ester 1,2,4,7-Tetrahydro-5-methyl-2-oxo-7-[2-(trifluoromethyl)phenyl]pyrazolo[1,5-a]pyrimidine-6-carboxylic acid, ethyl ester 7-(4-Benzofurazanyl)-1,2,4,7-tetrahydro-5-methyl-2-oxo-1-(2-propenyl)pyrazolo[1,5-a]pyrimidine-6-carboxylic acid, ethyl ester 7-(2-Chloro-3-nitrophenyl)-1,2,4,7-tetrahydro-5-methyl-1-[2-[methyl(phenylmethyl)amino]ethyl]-2-oxopyrazolo[1,5-a]pyrimidine-6-carboxylic acid, ethyl ester 1-[2-(Dimethylamino)ethyl]-1,2,4,7-tetrahydro-5-methyl-7-(3-nitrophenyl)-2-oxopyrazolo[1,5-a]pyrimidine-6-carboxylic acid, 1-methylethyl ester 1,2,4,7-Tetrahydro-5-methyl-7-[2-(methylthio)-3-pyridinyl]-2-oxopyrazolo[1,5-a]pyrimidine-6-carboxylic acid, ethyl ester 1,2,4,7-Tetrahydro-5-methyl-7-(3-nitrophenyl)-2-oxo-1-[2-[4-(phenylmethyl)-1-piperazinyl]ethyl]-pyrazolo[1,5-a]pyrimidine-6-carboxylic acid, 1-methylethyl ester 7-(2,3-Dichlorophenyl)-1,2,4,7-tetrahydro-5-methyl-2-oxo-1-[2-(tetrahydro-4H-1,4-thiazin-4-yl)ethyl]-pyrazolo[1,5-a]pyrimidine-6-carboxylic acid, ethyl ester 1-Acetyl-7-(2,3-dichlorophenyl)-1,2,4,7-tetrahydro-5-methyl-2-oxopyrazolo[1,5-a]pyrimidine-6-carboxylic acid, ethyl ester 1,2,4,7-Tetrahydro-5-methyl-1-(2-methyl-1-oxopropyl)-7-(2-nitrophenyl)-2-oxopyrazolo[1,5-a]pyrimidine-6-carboxylic acid, ethyl ester 1,2,4,7-Tetrahydro-5-methyl-2-oxo-1-(1-oxopropyl)-7-[2-(trifluoromethyl)phenyl]pyrazolo[1,5-a]pyrimidine-6-carboxylic acid, ethyl ester 7-(2-Chloro-3-nitrophenyl)-1-[3-(dimethylamino)-1-oxopropyl]-1,2,4,7-tetrahydro-5-methyl-2-oxopyrazolo[1,5-a]pyrimidine-6-carboxylic acid, ethyl ester 1-Benzoyl-1,2,4,7-tetrahydro-5-methyl-7-(3-nitrophenyl)-2-oxopyrazolo[1,5-a]pyrimidine-6-carboxylic acid, 2-[methyl(phenylmethyl)amino]ethyl ester 7-(Benzofurazan-4-yl)-1,2,4,7-tetrahydro-5-methyl-1-[3-[methyl(phenylmethyl)amino]-1-oxopropyl]-2-oxopyrazolo[1,5-a]pyrimidine-6-carboxylic acid, methyl ester 1-[(Dimethylamino)acetyl]-1,2,4,7-tetrahydro-5-methyl-7-[2-(methylthio)-3-pyridinyl]-2-oxopyrazolo[1,5-a]pyrimidine-6-carboxylic acid, ethyl ester 1,2,4,7-Tetrahydro-5-methyl-1-[4-[methyl(phenylmethyl)amino]-1-oxobutyl]-7-(3-nitrophenyl)-2-oxopyrazolo[1,5-a]pyrimidine-6-carboxylic acid, 1-methylethyl ester.

What is claimed is:

1. A compound having the formula

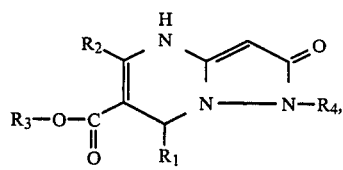

or a pharmaceutically acceptable salt thereof wherein $R_1$ is aryl;

$R_2$ is hydrogen, alkyl, alkenyl, alkynyl, cycloalkyl, aryl, $-(CH_2)_n-Y_1$, or halo substituted alkyl;

$R_3$ is hydrogen, alkyl, cycloalkyl, aryl, $-(CH_2)_n-Y_2$, $-(CH_2)_p-Y_3$, or halo substituted alkyl;

$R_4$ is hydrogen, alkyl, alkenyl, alkynyl, $-(CH_2)_n-Y_2$, $-(CH_2)_p-Y_3$, halo substituted alkyl, or

Y$_1$ is cycloalkyl, aryl, hydroxyl, alkoxy, aryl—(CH$_2$)$_m$—O—, mercapto, alkylthio, aryl—(CH$_2$)$_m$—S—, amino, substituted amino, carbamoyl, (substituted amino)—C(=O)—, carboxyl, alkoxycarbonyl, alkyl—C(=O)—, aryl—(CH$_2$)$_m$—C(=O)—, alkyl—C(=O)—O— or aryl—(CH$_2$)$_m$—C(=O)—O—;

Y$_2$ is cycloalkyl, aryl, carbamoyl, (substituted amino)—C(=O)—, carboxyl, alkoxycarbonyl, alkyl—C(=O)—, or aryl—(CH$_2$)$_m$—C(=O)—;

Y$_3$ is hydroxyl, alkoxy, aryl—(CH$_2$)$_m$—O—, mercapto, alkylthio, aryl—(CH$_2$)$_m$—S—, alkyl—C(=O)—O—, aryl—(CH$_2$)$_m$—C(=O)—O—, amino, or substituted amino;
Y$_4$ is alkyl, cycloalkyl, aryl, —(CH$_2$)$_n$—Y$_1$ or halo substituted alkyl;
m is 0 or an integer of 1 to 6;
n is an integer of 1 to 6; and
p is an integer of 2 to 6;
wherein the term "cycloalkyl" refers to cycloalkyl groups having 3,4,5,6 or 7 carbon atoms;
the term "aryl" refers to phenyl and phenyl substituted with one, two or three alkyl, alkoxy, alkylthio, halo, nitro, cyano, hydroxy, amino, alkylamino, dialkylamino, trifluoromethyl, isothiocyanato, isocyanato, or difluoromethoxy groups; and
the term "substituted amino" refers to a group of the formula —NZ$_1$Z$_2$ wherein Z$_1$ is hydrogen, alkyl or aryl—(CH$_2$)$_m$— and Z$_2$ is alkyl or aryl—(CH$_2$)$_m$— or Z$_1$ and Z$_2$ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, or 1-pyrrolidinyl, 1-piperidinyl, or 1-azepinyl substituted with alkyl, alkoxy, alkylthio, halo, trifluoromethyl or hydroxy.

2. A compound in accordance with claim 1 wherein R$_1$ is aryl.

3. A compound in accordance with claim 2 wherein R$_1$ is 2,3-dichlorophenyl.

4. A compound in accordance with claim 2 wherein R$_1$ is 3-nitrophenyl.

5. A compound in accordance with claim 1 wherein R$_2$ is alkyl.

6. A compound in accordance with claim 5 wherein R$_2$ is methyl.

7. A compound in accordance with claim 1 wherein R$_3$ is alkyl.

8. A compound in accordance with claim 7 wherein R$_3$ is ethyl.

9. A compound in accordance with claim 7 wherein R$_3$ is 1-methylethyl.

10. A compound in accordance with claim 1 wherein R$_4$ is hydrogen.

11. A compound in accordance with claim 1 wherein R$_4$ is

12. A compound in accordance with claim 1 wherein R$_4$ is alkyl, alkenyl, alkynyl, —(CH$_2$)$_n$—Y$_2$, —(CH$_2$)$_p$—Y$_3$ or halo substituted alkyl.

13. A compound in accordance with claim 1 wherein R$_1$ is aryl, R$_2$ is alkyl, R$_3$ is alkyl and R$_4$ is hydrogen.

14. The compound in accordance with claim 1, 7-(2,3-dichlorophenyl)-1,2,4,7-tetrahydro-5-methyl-2-oxopyrazolo[1,5-a]pyrimidine-6-carboxylic acid, ethyl ester.

15. The compound in accordance with claim 1, 1,2,4,7-tetrahydro-5-methyl-7-(3-nitrophenyl)-2-oxopyrazolo[1,2-a]pyrimidine-6-carboxylic acid, 1-methylethyl ester.

16. The compound in accordance with claim 1, 1,2,4,7-tetrahydro-5-methyl-7-(3-nitrophenyl)-2-oxo-1-(phenylmethyl)pyrazolo[1,5-a]pyrimidine-6-carboxylic acid, 1-methylethyl ester.

17. The compound in accordance with claim 1, 1-benzoyl-1,2,4,7-tetrahydro-5-methyl-7-(3-nitrophenyl)-2-oxopyrazolo[1,5-a]pyrimidine-6-carboxylic acid, 1-methylethyl ester.

18. A method for reducing the blood pressure of a mammalian host in need thereof which comprises administering to said host an effective amount of a compound having the formula

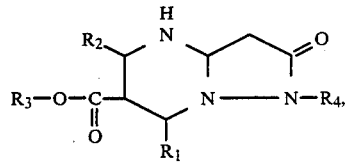

or a pharmaceutically acceptable salt thereof wherein
R$_1$ is aryl;
R$_2$ is hydrogen, alkyl, alkenyl, alkynyl, cycloalkyl, aryl, —(CH$_2$)$_n$—Y$_1$, or halo substituted alkyl;
R$_3$ is hydrogen, alkyl, cycloalkyl, aryl, —(CH$_2$)$_n$—Y$_2$, —(CH$_2$)$_p$—Y$_3$, or halo substituted alkyl;
R$_4$ is hydrogen, alkyl, alkenyl, alkynyl, —(CH$_2$)$_n$—Y$_2$, —(CH$_2$)$_p$—Y$_3$, halo substituted alkyl, or

Y$_1$ is cycloalkyl, aryl, hydroxyl, alkoxy, aryl—(CH$_2$)$_m$—O—, mercapto, alkylthio, aryl—(CH$_2$)$_m$—S—, amino, substituted amino, carbamoyl, $$\text{(substituted amino)}-\overset{\overset{O}{\|}}{C}-, \text{ carboxyl, alkoxycarbonyl,}$$

$$\text{alkyl}-\overset{\overset{O}{\|}}{C}-, \text{ aryl}-(CH_2)_m-\overset{\overset{O}{\|}}{C}-, \text{ alkyl}-\overset{\overset{O}{\|}}{C}-O- \text{ or}$$

$$\text{aryl}-(CH_2)_m-\overset{\overset{O}{\|}}{C}-O-;$$

$Y_2$ is cycloalkyl, aryl, carbamoyl, $$\text{(substituted amino)}-\overset{\overset{O}{\|}}{C}-, \text{ carboxyl, alkoxycarbonyl,}$$

$$\text{alkyl}-\overset{\overset{O}{\|}}{C}-, \text{ or aryl}-(CH_2)_m-\overset{\overset{O}{\|}}{C}-;$$

$Y_3$ is hydroxyl, alkoxy, aryl—$(CH_2)_m$—O—, mercapto, alkylthio, aryl—$(CH_2)_m$—S—, $$\text{alkyl}-\overset{\overset{O}{\|}}{C}-O-, \text{ aryl}-(CH_2)_m-\overset{\overset{O}{\|}}{C}-O-,$$

amino, or substituted amino;

$Y_4$ is alkyl, cycloalkyl, aryl, —$(CH_2)_n$—$Y_1$ or halo substituted alkyl;

m is 0 or an integer of 1 to 6;

n is an integer of 1 to 6; and p is an integer of 2 to 6;

wherein the term "cycloalkyl" refers to cycloalkyl groups having 3, 4, 5, 6 or 7 carbon atoms;

the term "aryl" refers to phenyl and phenyl substituted with one, two or three alkyl, alkoxy, alkylthio, halo, nitro, cyano, hydroxy, amino, alkylamino, dialkylamino, trifluoromethyl, isothiocyanato, isocyanato, or difluoromethoxy groups; and the term "substituted amino" refers to a group of the formula —$NZ_1Z_2$ wherein $Z_1$ is hydrogen, alkyl or aryl—$(CH_2)_m$— and $Z_2$ is alkyl or aryl—$(CH_2)_m$— or $Z_1$ and $Z_2$ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, or 1-pyrrolidinyl, 1-piperidinyl, or 1-azepinyl substituted with alkyl, alkoxy, alkylthio, halo, trifluoromethyl or hydroxy.

* * * * *